United States Patent [19]
Chinn

[11] Patent Number: 5,647,868
[45] Date of Patent: Jul. 15, 1997

[54] CRYOSURGICAL INTEGRATED CONTROL AND MONITORING SYSTEM AND METHOD

[76] Inventor: Douglas Owen Chinn, 65 N. 1st Ave., Ste. 101, Arcadia, Calif. 91006

[21] Appl. No.: 430,294

[22] Filed: Apr. 28, 1995

Related U.S. Application Data

[63] Continuation of Ser. No. 190,264, Feb. 2, 1994, abandoned.
[51] Int. Cl.$^6$ .................................................. A61B 17/36
[52] U.S. Cl. ........................ 606/21; 606/23; 128/660.03
[58] Field of Search ........................ 606/20–26; 607/101, 607/102, 104, 105; 128/660.03

[56] References Cited

U.S. PATENT DOCUMENTS

| | | | |
|---|---|---|---|
| 3,948,269 | 4/1976 | Zimmer | 606/24 |
| 4,306,568 | 12/1981 | Torre | 606/20 X |
| 4,802,475 | 2/1989 | Weshahy | 606/21 |
| 5,049,147 | 9/1991 | Danon | 606/10 |
| 5,163,432 | 11/1992 | Ueno et al. | 606/11 |
| 5,403,309 | 4/1995 | Coleman et al. | 606/20 |

OTHER PUBLICATIONS

Onik et al., "Transrectal Ultrasound–Guided Percutaneous Cryosurgery," LJ–Cancer, vol. 72, No. 4, 1992.

Onik et al. Transrectal Ultrasound–Guided Percutaneous Radical Cryosurgical Ablation of the Prostate. (Cancer, Jun. 28, 1993.) 1291–1299.

Onik et al. US Characteristices of Frozen Prostate[1]. (Radiology Sep. 1988). 629–631.

Seidmon, Dr. James, E. Negotiating the Complications of Radical Prostatectomy (Contemporary Urology Mar. 1993) 68–78.

Gage, Dr. Andrew A. Cryosurgery in the Treatment of Cancer (Surgery, Gynecology & Obstetrics Jan. 1992). 73–88.

Encyclopedia of Medical Devices and Instrumentation, vol. 2; (1988) pp. 893–908.

Gage, Dr. Andrew A., A Comparison of Instrument Methods of Monitoring Freezing in Cryosurgery (Dermatol. Surg. Oncol. Mar. 1983) 209–214.

Price, Dr. Ely, Use of Thermocouples in Cryosurgery (J. Dermatol. Surg. Oncol. Mar. 1983) 215–218.

*Primary Examiner*—Lee S. Cohen
*Assistant Examiner*—Bryan K. Yarnell
*Attorney, Agent, or Firm*—Morland C. Fischer; James E. Hawes

[57] ABSTRACT

The present cryosurgical system and method accurately locates relative to a defined internal area of a living body, an ultrasonic probe and, using stereotactic guide, a series of cooling probes and temperature probes, then presents in the same visual field an integrated ultrasonic display and temperature display to assist the surgeon in accurately sculpting and limiting the field of cooling.

21 Claims, 5 Drawing Sheets

CRYOSURGICAL INTEGRATED CONTROL AND MONITORING SYSTEM AND METHOD

This application is a continuation, of application Ser. No. 08/190,264, filed Feb. 2, 1994, now abandoned.

INTRODUCTION

The present invention relates to a cryosurgical integrated control monitoring system, method, probe and guide, particularly one employing a plurality of cryogenic probes and temperature probes, accurately placed in part by use of a unique guide, to effect the controlled cooling, usually beyond freezing, of a defined internal area of a living body.

Cryosurgical procedures have been known and used for decades. In general, using earlier techniques it has been difficult or impossible to sculpt a particular temperature gradient, or frozen area, especially within a living body. In recent years a cryogenic system has been introduced that provides a plurality of cryogenic probes designed to apply extremely low temperatures to a small zone of tissue at their tips. By accurately placing these probes and controlling the cooling applied to the tissue by each probe, it is possible to sculpt particular shapes or zones of cooling or freezing within a living body. In the recent past, some of these probes have been placed using an ultrasonic system and a stereotactic guide. The ultrasonic system also permits monitoring, at least in a general fashion, of the resulting frozen area produced by the cryogenic probes.

Cryogenic techniques appear to offer significant promise for various surgical procedures. For example, by using them in general it is possible to freeze an entire gland, such as the prostate gland. This freezing appears to not only kill the gland, and any cancerous regions it may incorporate, but also to freeze and kill cancerous extensions adjacent to the gland. Because of this, cryogenic procedures may offer significant therapeutic advantages.

But cryosurgery offers significant challenges. For prostate cryosurgery, ultrasound is currently used to monitor and control the freezing process. When an ice ball forms, ultrasonically it becomes black, and only the leading edge can be seen on ultrasound. It appears as a white line and represents 0° C.; the black area just behind the white line represents −15° C. But water can supercool to between −15° C. to −44° C. without freezing, meaning that cellular death is not absolute until −44° C. is obtained. However, ultrasound only images the interface between water and ice, and there can be supercooled tissue inside the black, ultrasonically imaged ice ball. Also, there is acoustic shadowing, and the posterior side of the ice ball will cast a shadow laterally and anteriorly; thus, the true lateral and anterior extent of the ice ball will not be seen. Therefore, it is important to be able to monitor the temperature at the edges of the tissue to be treated to ensure that the target (fatal) temperature is attainable in some areas, and then a second freeze, or pull back of the probes, is necessary. It is also important not to freeze other structures adjacent to the tissue or organ being treated. For example, posterior to the prostate is the anterior rectal wall. Freezing into the rectal wall will cause an urethrorectal fistula.

In summary, while cryosurgical procedures offer real promise in certain applications, to realize that promise it is essential to accurately sculpt the desired freezing zone so as to envelope all of the desired area with the target temperature reduction but to not adversely effect adjacent structures.

A major object of the present invention is to provide a cryosurgical integrated control and monitoring system and method to permit adequate freezing zones to be accurately sculpted within a living body without adversely effecting adjacent zones or structures. Another object of the present invention is to provide a temperature probe, preferably a percutaneous probe, that may be accurately located and employed to monitor the temperature within a small, defined zone within the body. A further object is to provide an improved stereotactic guide to assist in the accurate placement of cryogenic cooling and temperature monitoring probes. Another object is to provide a system with an integrated display to enable a surgeon to accurately and effectively control all significant aspects of a cryosurgical procedure within a living body. These and other objects of the present invention will be apparent to those skilled in this field from the following description of preferred embodiments.

BRIEF SUMMARY OF THE INVENTION

The invention provides a cryosurgical system and method for treating a defined internal region of a living body. It incorporates and employs a unique temperature probe and a stereotactic guide for assisting in accurately placing the cryogenic and temperature probes within the body to be treated.

The cryosurgical system includes means for cooling the defined internal area and means for measuring the temperature of the defined internal area as it is cooled. An ultrasonic subsystem is employed to illuminate the defined internal area being cooled and displays an ultrasonic image produced as a result of the ultrasonic illumination. The system also displays the temperature of the defined internal area being cooled thereby to permit the cooling to be accurately controlled. Preferably the ultrasonic image and the temperature data are displayed in the same visual field, and the temperature display presents the measured temperature at successive moments over a recent time interval including the current interval. Also, preferably the means for measuring temperature includes a plurality of percutaneous temperature probes and the cooling means includes a plurality of cooling probes, all to permit the cryogenic system to cool and monitor a defined internal area of most any desired shape within a living body. Further, preferably the cryogenic system includes means to maintain the temperature of at least a portion of the living body within the defined internal area and means to record the displayed ultrasonic image and temperature information.

The cryogenic method for treating a defined internal region of a living body includes the steps of cooling the defined internal area of the body as the temperature is measured, and ultrasonically illuminating the defined internal area then displaying an ultrasonic image of the illuminated area as it is being cooled. It may also include displaying the ultrasonic image and temperature information in the same visual field. The temperature information may be displayed at each successive moment over a recent time interval including a current interval. Further, it may include the steps of recording the displayed ultrasonic image and temperature information and, if desired, maintaining the temperature of at least a portion of the living body within the defined internal area.

The temperature probe preferred for use in the present invention is designed to measure the temperature of a small defined internal area of a living body. The probe includes an elongated hollow tube having two ends, the two being closed at its distal end. A canister is attached to the proximal end of the tube. A device for measuring temperature and producing an electrical signal is received within the tube and is positioned adjacent to the distal end of the tube. An electrical conductor extends from the temperature measuring device through the tube and canister to provide, external of the probe, an electrical signal representative of the temperature in the region adjacent the tip of the probe. Preferably the probe also includes means for sealing the canister and probe so that they may be sterilized and are suitable for use percutaneously in measuring the temperature of an internal area of a living body without producing infection. Also, preferably at least the distal end of the tube is a good thermal conductor. The probe may further include a trocar, the inner diameter of which is slightly larger than the outer diameter of the elongated hollow tube to assist in accurately placing the temperature probe within a living body. Further, the tube may include an echogenic coating or markings to aid in its ultrasonic visualization and placement, or incorporate an echogenic marking defining the region of the tube within which is positioned the temperature measuring device. In the preferred embodiment, the temperature measuring device is a T-type thermocouple.

The improved stereotactic guide preferably employed in the cryogenic system is designed to assist in accurately placing cryogenic probes and temperature probes within a defined internal area of a living body. The guide includes a frame with a frame block moveable along the frame, the frame block receiving at least one guide bar. The guide bar is movably attached to the frame block and has, at one end, a guide block. The guide block includes means for accurately guiding a temperature probe or a cryogenic probe along a predefined path. The guide also includes means for orienting the guide block relative to a defined location in the living body. In the preferred construction of the stereotactic guide, the orienting means is a sleeve for receiving the cylindrical body of an ultrasonic probe that is passed through an orifice in the body and employed to illuminate the defined internal area to be treated. Preferably the frame block is adjustable and may be fixed a defined distance from the orienting means, and the guide bar is moveable through the frame block along an axis generally parallel to that defined by the orienting means.

BRIEF DESCRIPTION OF THE DRAWING

The invention will be further described with reference to the accompanying drawings in which.

DETAILED DESCRIPTION

Figure 1:
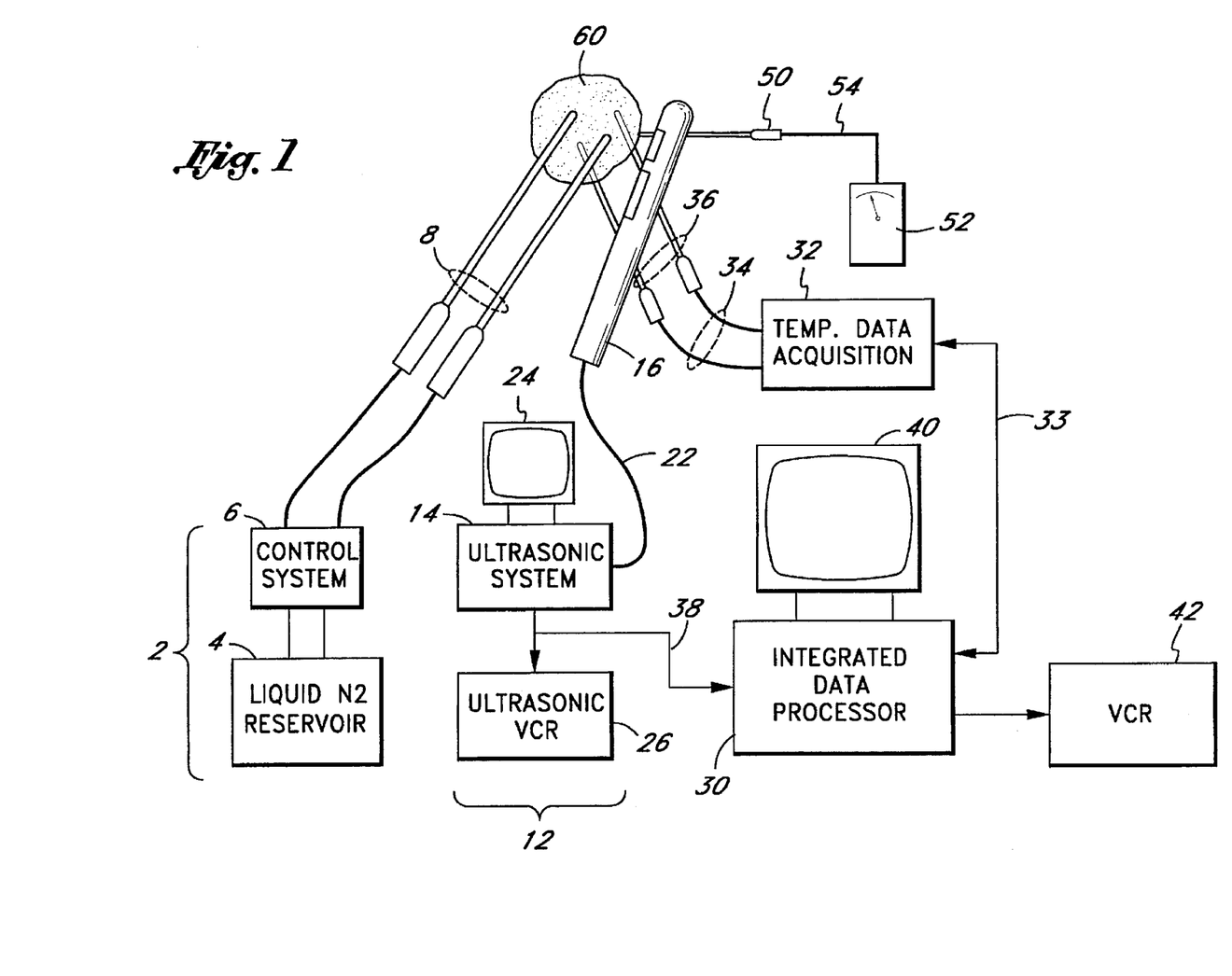
FIG. 1 is a schematic diagram of the cryosurgical system.
Figure 2:
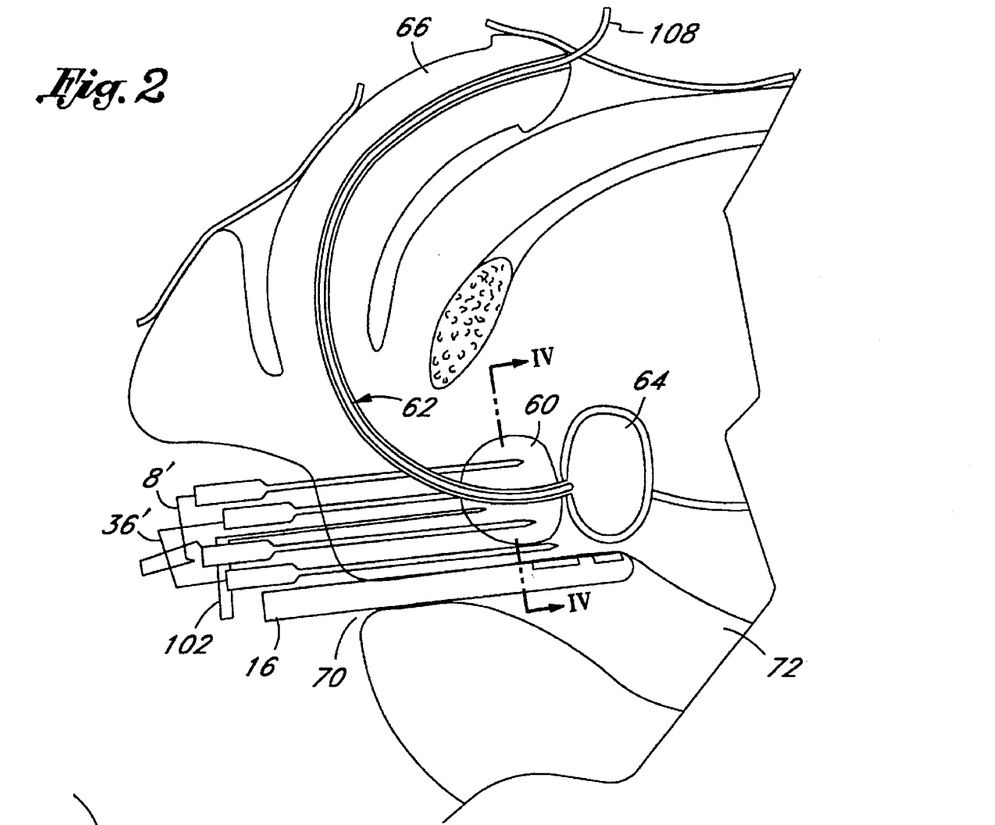
FIG. 2 is a cross-sectional view of a portion of a human body showing portions of the cryosurgical system in place.
Figures 3, 4:
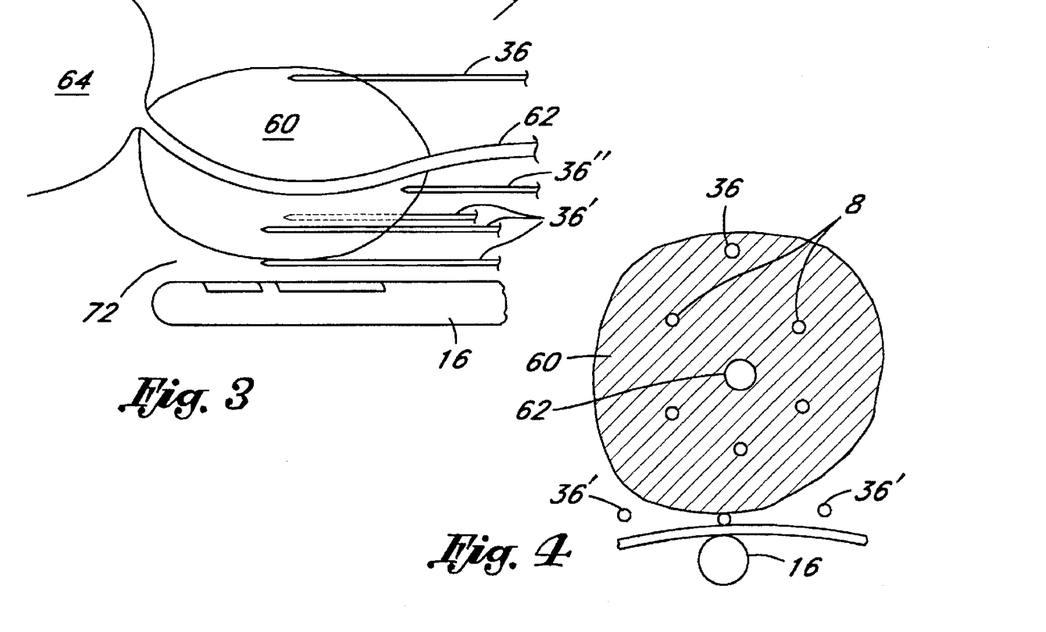
FIG. 3 is a lateral view of a portion of a human body showing positions of the cryosurgical system in place.
FIG. 4 is a cross-sectional view taken on lines IV—IV of FIG. 2.

The various components of the preferred cryosurgical system for treating a defined internal area of a living body are shown in FIG. 1. FIGS. 2 and 3 illustrate the placement of portions of the FIG. 1 system, particularly its various probes, in a defined region of a human body, specifically in a prostate gland. Of course, the system could be employed to cryogenically treat most any other defined internal area of a living body, such as to treat liver, breast, eyeball, or brain tissue or tonsils for example.

The cryosurgical system includes various major components. Specifically, as shown in FIG. 1, it incorporates a cryogenic cooling system 2 such as the AccuProbe System of Cryomedical Sciences Inc. located in Rockville, Md. That system controls the circulation of liquid nitrogen from a reservoir 4 through a control system 6 to a plurality of cryogenic probes 8. In the AccuProbe System these probes are 3 mm. in diameter and are made of 304 stainless steel. While only two probes are shown in FIG. 1, the system is capable of separately controlling the flow to five probes and, in many cryogenic surgical operations, all five probes will be used.

The cryosurgical system also includes an ultrasonic system 12 such as that made by Aloka Ultrasound of Wallingsford, Conn. The ultrasonic system generally includes an ultrasonic signal generator and processor 14 that is connected to an ultrasonic probe 16 to cause it to generate ultrasonic vibrations at window 18 and to receive those vibrations at window 20. These received vibrations are converted to electrical vibrations that are supplied to processor 14 over connector 22. Connected to processor 14 is a display device 24, such as a CRT monitor, and a recording device 26 such as a video cassette recorder.

The cryogenic system further includes an integrated data processor 30 connected to a temperature data acquisition system 32 over line 33. The temperature data acquisition system also electrically isolates the patient from the rest of the electronics. The data processor, in the current version of the system, is a Dell computer with an Intel 486 DXS 33 CPU, 8 megabytes of RAM, a 200 megabyte hard drive, an appropriate 3½", 1.44 megabyte floppy drive, and a tape backup. The data acquisition system in turn is connected by lines 34 to temperature probes 36. Again, while only two temperature probes are shown in the preferred system a greater number of probes often will be used. The data processor 30 is also electrically connected to the ultrasonic signal processor 14 through line 38 thereby to receive ultrasonic image information. A display device 40, such as a CRT monitor, is connected to the data processor 30 to display an image which preferably incorporates both the ultrasonic image and temperature data in a fashion that will be described shortly. The monitor 40 preferably is a SVGA non-interlaced monitor driven by a Snap Plus video card offered by Cardinal Technology located in Lancaster, Pa., this card being received the data processor 30. A recorder 42, such as a VCR, is also connected to the data processor 30 to receive and record the visual information displayed on monitor 40 for future reference if desired.

The data processor may be loaded with appropriate software, including DOS 6.0, MicroSoft Windows 3.1 and the Lab View program offered by National Instruments of Austin, Tex. This program is appropriately initiated to present the information subsequently described herein.

Finally, the preferred embodiment of the cryosurgical system includes one or more temperature probes 50 that are connected to one or more hand held, battery powered meters 52 (such as the meter offered by Omega Engineering Inc. of Stanford, Conn.) through one or more lines 54 to insure that, should operational problems be encountered with either the ultrasonic system 12 or the temperature data acquisition system 32, or with data processor 30 or monitor 40, the operator of the system will still be able to monitor temperatures sufficiently to close down the cryogenic treatment in a controlled fashion. Conveniently, these meters may be mounted on or received in an appropriate holder that supports them on or adjacent monitor 40 to be in the same visual field as the monitor's screen and to be easily watched by the system operator.

As previously indicated, FIGS. 2 and 3 illustrate use of the system to treat a prostate gland. FIG. 2 is a vertical cross-section through the medial plane of the lower torso region of a human male; FIG. 3 is a lateral view through that region. In general, these views illustrate a prostate gland 60 surrounding a urethral tube 62 extending from bladder 64 to the tip of penis 66. Also shown is anus 70 and rectum 72. The cryogenic cooling probes 8 have been percutaneously placed into target locations within the prostate gland 60 preferably using a stereotactic guide which will be described shortly. Also, temperature probes 36 have been placed adjacent to the prostate gland, optionally using that stereotactic guide.

For a cryogenic surgical procedure, the preferred placement of the cryogenic probes and temperature probes is shown in FIG. 4, which is a cross-section taken on planes IV—IV of FIG. 2. The cryogenic probes 8 have been placed in the prostate gland 60 about the urethral tube 62 equally spaced about a target circle about half way between that tube and the outer surface of the gland. Preferably they are located to apply cryogenic cooling to the mid-portion of the gland, although if the gland is enlarged it may be necessary to first place the probes closer to the bladder, then later during the treatment to move them away from the bladder thereby to treat the remaining, apex portion of the gland. The temperature probes 36 have been placed in and about the gland generally as shown, with three temperature probes preferably being placed in the critical region between the prostate gland and the adjacent wall of the rectum 72. The ultrasonic probe 16 has been placed through the anus and oriented such that its windows lie along the wall of rectum 72 and face the prostate gland generally as shown in FIGS. 2 and 3.

In general, during a cryosurgical treatment of a defined internal area of a living body the cryogenic probes are employed to cool that area to a fatal temperature, which generally is between −15° C. and −44° C. It is important to monitor the temperature of the region surrounding the defined internal area to ensure that the target temperature (usually a fatal temperature) is attained. As cooling occurs, an ice ball will form in the area being cooled. To prevent this cooling from extending to other regions of the body it is necessary to monitor temperatures accurately. In particular, when treating a prostate gland, it is important to monitor the temperature between the gland and the wall of the rectum to ensure that the wall of the rectum is not cooled to a point where its viability is challenged, for this may result in a fistulae in the rectum wall. For that reason, one of temperature probes 36' is placed posterior to the gland and anterior to the wall of the rectum. It is also important to monitor growth of the ice ball as it forms in the prostate gland during cryogenic treatment to make sure that it extends from the base of the gland adjacent bladder 64 to its apex. Preferably temperature probe 36" is placed for that purpose.

Figure 5:
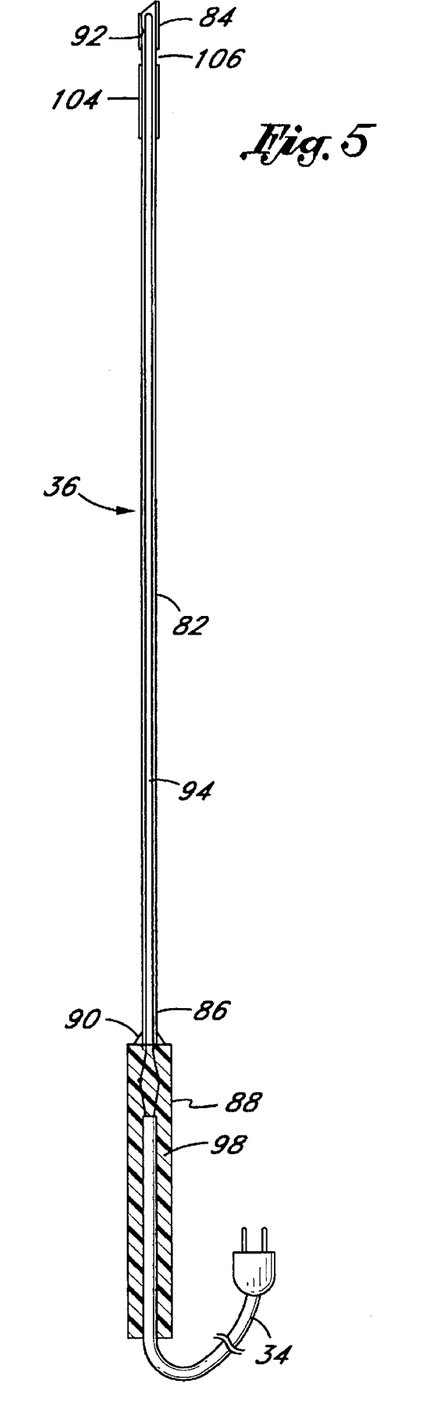
FIG. 5 is a longitudinal cross-sectional view of one preferred construction of a temperature probe.

The preferred construction of the temperature probe 36 is shown in FIG. 5. The probe consists of, preferably, a length of hypodermic tubing 82 preferably on the order of 0.035 inches in outer diameter (i.e. 18 gauge tubing) made of 316 stainless steel. It conveniently may be on the order of 8–9 inches long. One typical way to make such a probe is to place the necessary elements in a tube, then stretch the tube and included elements down to the desired outer diameter. Since this can result in a flexible tube, if such a construction technique is used preferably the resulting tube is placed in a layer, tube of appropriate rigidity. At its distal end 84 it is closed, such as by a small amount of 316 stainless steel solder, and sharpened for percutaneous penetration into a defined area of a living body as previously indicated. The proximal end 86 of the tubing is received in a hollow cylindrical canister 88 also preferably made of 316 stainless steel. This canister may be on the order of ¼ inch in diameter and 2½ inches long. The proximal end of the tubing 82 preferably is attached to the end of canister 88 by a slug of cadmium free silver solder 90. A T-type thermocouple 92 is positioned in the distal end of tubing 82 and is connected by wires 94 to cable 34 within the canister. After this connection has been made, and the thermocouple tested, preferably the canister is filled with an epoxy 98 or other suitable material. Cable 34 extends to an appropriate plug for connection to the temperature data acquisition system 32. By this construction, the temperature probe may be cold sterilized using Cidex without degradation. It may also be gas sterilized by ethylene oxide [Eto].

Figure 6:
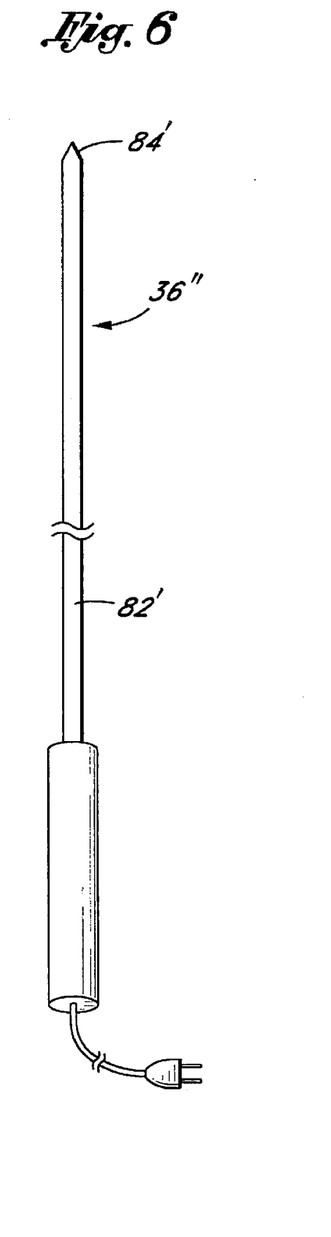
FIG. 6 is a longitudinal cross-sectional view of another preferred construction of a temperature probe.

The probe shown in FIG. 5 is appropriate for placement laterally of the prostate gland such as shown in FIGS. 2–4. It is also desirable to have a probe designed for placement at the apex of the gland, such as probe 36" shown in FIG. 3. A construction of such a probe 36" is illustrated in FIG. 6. In general this construction is identical to that of the probe shown in FIG. 5 except that end 84' terminates in point, the OD of the tubing is 0.040 or 0.065 inches as desired, and the length of tubing 82' is on the order of 5–6".

Placement of the temperature probe within a living body may be effected in various ways, many of which are conventional to cryosurgical procedures. For example, using the ultrasonic probe and an 18 gauge Onik needle with a stylet is located and directed free hand or by an appropriate stereotactic guide, such as subsequently described and shown in FIGS. 7 and 8 herein. The needle is appropriately directed to a desired location within or adjacent to the gland, after which the stylet is withdrawn and a temperature probe inserted through the needle to the desired location as appropriate. In general, the trocar or Onik needle (used to placed the cryo probes) consists of a hollow tube whose inner diameter is slightly larger than the outer diameter of tubing 82. Normally it is inserted percutaneously in the body, then the probe passed through it to cause the distal end 92 to project slightly beyond the end of the trocar, specifically a distance to unshield the thermocouple 92. In a preferred construction, the thermocouple is approximately 1 to 2 millimeters long. To ensure that the thermocouple is unshielded, and to aid in ultrasonic visualizations of the probe, preferably at least the distal portion of tubing 82 includes an echogenic coating 104 to enhance its ultrasonic image, and is marked by break 106 to identify the distal portion of tubing 82 that houses the thermocouple 84. The base portion 86 of the probe may be marked with graduations, and these graduations employed by the system operator when the tip of the probe is seen ultrasonically to begin to extend beyond the trocar, thereby to ensure that a sufficient length of the probe's tip is extended past the tip of the trocar.

When cryosurgically treating a prostate gland it is often desirable to circulate a warming fluid through the urethral tube. To this end, a catheter 108 is inserted through the penis and employed to circulate water warmed to about 44 degrees centigrade through the urethral tube in the prostate to prevent a fatal temperature from being reached in its wall. An esophageal thermocouple also may be used to monitor the patient's body temperature and detect hypothermia.

Figures 7, 8:
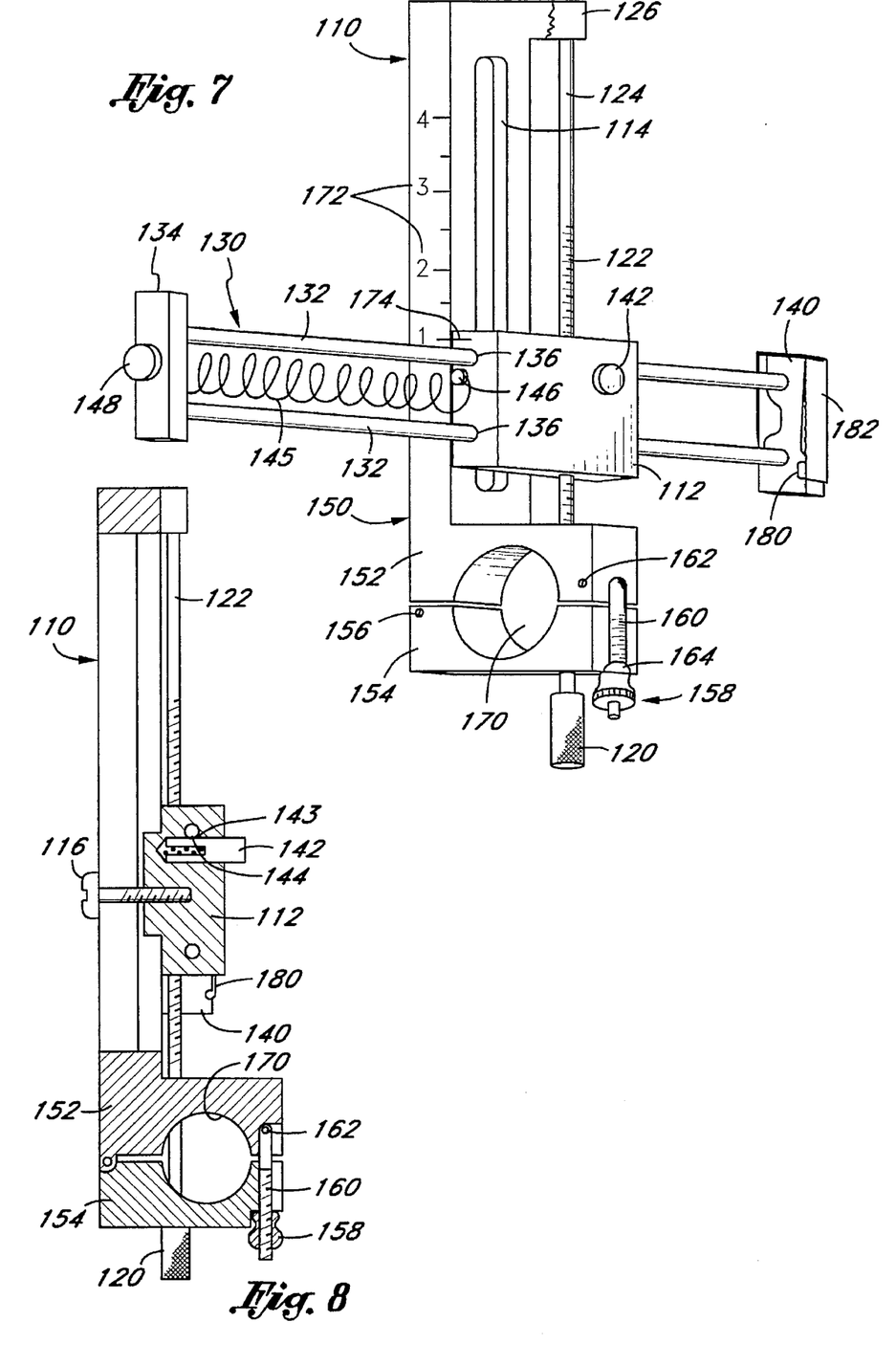
FIG. 7 is a perspective view of the stereotactic guide.
FIG. 8 is an elevational view of the stereotactic guide.

To place the various probes, particularly the cryo probes, preferably an improved stereotactic guide, such as shown in FIGS. 7 and 8, is employed. This guide consists of a frame 110 on which is mounted a frame block 112. More particularly, the frame 110 incorporates a slot 114 that receives the shaft of a screw 116 (shown in FIG. 8 and preferably of plastic) the shaft of which is threaded into frame block 112. The head of screw 116 slides along the back surface of frame 110. Such movement conveniently may be effected using knurled knob 120 attached to a threaded shaft 122 that extends through a boss on frame block 112. The end 124 of the shaft is received and captured in an opening in boss 126 projecting from frame 110. Thus, by rotating knob 120 it is possible, through the threaded engagement of shaft 122 with frame block 112, to cause the frame block to slide up and down along frame 110.

A guide bar 130, consisting of rods 132 held in a parallel spaced relationship by a proximal block 134, is received in and slides through openings 136 in frame block 112. The distal ends of rods 132 are captured in a guide block 140. A spring biased button 142 is received in block 112 and includes a deatent 143 that engages a notch 144 in rod 132 to hold the guide bar in a retracted orientation as generally shown in FIG. 8. A spring 145 is connected to the frame block by clamp 146 and to the proximal block 134 by clamp 148. The spring tends to pull proximal block 134 toward frame block 112, but that motion is prevented while button 142 engages the notch in rod 132 as described.

At the base portion of frame 110 is a positioning block 150. It consists of an upper shell 152 and a lower shell 154 that are pivotally connected to one another by pivot pin 156. The shells are clamped to one another by lock nut 158 received on threaded shaft 160 that in turn is pivotally attached to upper shell 152 by pivot pin 162, the threaded shaft being received in a recess in both upper shell 152 and lower shell 154 as shown. Preferably the enlarged base 164 of lock nut 158 is received in an appropriately formed recess that encompasses more than a half circle of base 164, thereby to capture lock nut 158 and prevent it from moving out of this recess until it is turned down on threaded shaft 160 a distance to clear the bottom surface of lower shell 154. By this arrangement, the attachments of the shells to one another may be loosened to enlarge cylindrical opening 170 in shells 152 and 154 without releasing shell 154.

Opening 170 is slightly smaller than the outer diameter of the ultrasonic probe 16. Accordingly, by loosening lock nut 158 the size of opening 170 may be enlarged sufficiently to permit the ultrasonic probe to be passed through opening 170 and into a portion of the body to be illuminated by the probe, such as through anus 70. When the ultrasonic probe has been appropriately positioned, lock nut 158 is turned down to clamp the upper and lower shells about the probe and to fix frame 110 relative to the probe. A series of graduations 172 are provided on the back surface of the frame to permit the location of frame block 112 to be accurately or reproducibly located and positioned on frame 110 using marking 174 provided on the back surface of the frame block, this positioning being effected by turning knurled knob 120 to cause its threaded shaft to drive frame block 112 up and down as described.

Guide block 140 includes a cylindrical opening 180 in its face that is closed by a sheet metal slide 182 shaped to envelope the guide block and to be movable up and down along the guide block to expose or close cylindrical opening 180 as desired.

By this configuration of the improved stereotactic guide, the various cryoprobes and temperature probes that are desired to be used during the cryosurgical operation can each be accurately placed percutaneously within a body. Specifically, and again with reference to the prostate gland treatment generally illustrated in FIGS. 2 and 3, the guide is clamped around ultrasonic probe 16 and located to orient cylindrical opening 180 at various predetermined distances spaced from the ultrasonic probe. The probes are then passed through cylindrical opening 180, this opening for example guiding the shaft 82 of the temperature probe 36 along a path parallel to the ultrasonic probe to permit its accurate percutaneous placement within the body.

This placement is selected and monitored using the cryogenic system shown in FIG. 1. Specifically, in one approach first the ultrasonic probe is placed within the rectum and used to illuminate the prostate gland. To separate the rectal wall from the prostate gland, the tip of the ultrasonic probe may be moved and depressed against the posterior wall of the rectum—this tends to pull the rectum off the prostate [this technique is also utilized during freezing]. Using the Onik Dilator Set (Cook Urologic Co), 18 gauge needles with trocars are placed in various desired positions within the prostate gland. Five such needles are generally used; the stereotactic guide and ultrasound are employed to properly guide the needle placement. After each needle is placed, the trocar is removed, and a 0.032" diameter guide wire is passed through the needle and into the prostate with ultrasound monitoring. The needle is then backed off of the guide wire and removed. After all five guide wires are placed, dilators with backloaded sheaths are placed over each guide wire and ultrasonically guided and positioned into the prostate gland. Ultimately, five cryogenic probes will be passed through the sheaths into the prostate. After all the sheaths are in place, then the previously used 18 gauge needles with the trocars are ultrasonically, and with freehand, placed at the (1) right neurovascular bundle, (2) left neurovascular bundle, and (3) at the 6:00 o'clock position between the rectum and posterior prostate. The longer 0.035 thermocouples are then passed through the 18 gauge needles and into the desired depth, again using ultrasonic guidance. Two of the shorter thermocouples are placed freehand without the use of the 18 gauge needles, but with the use of ultrasound (4) at the apex and (5) anterior edge of the prostate.

Figure 9:
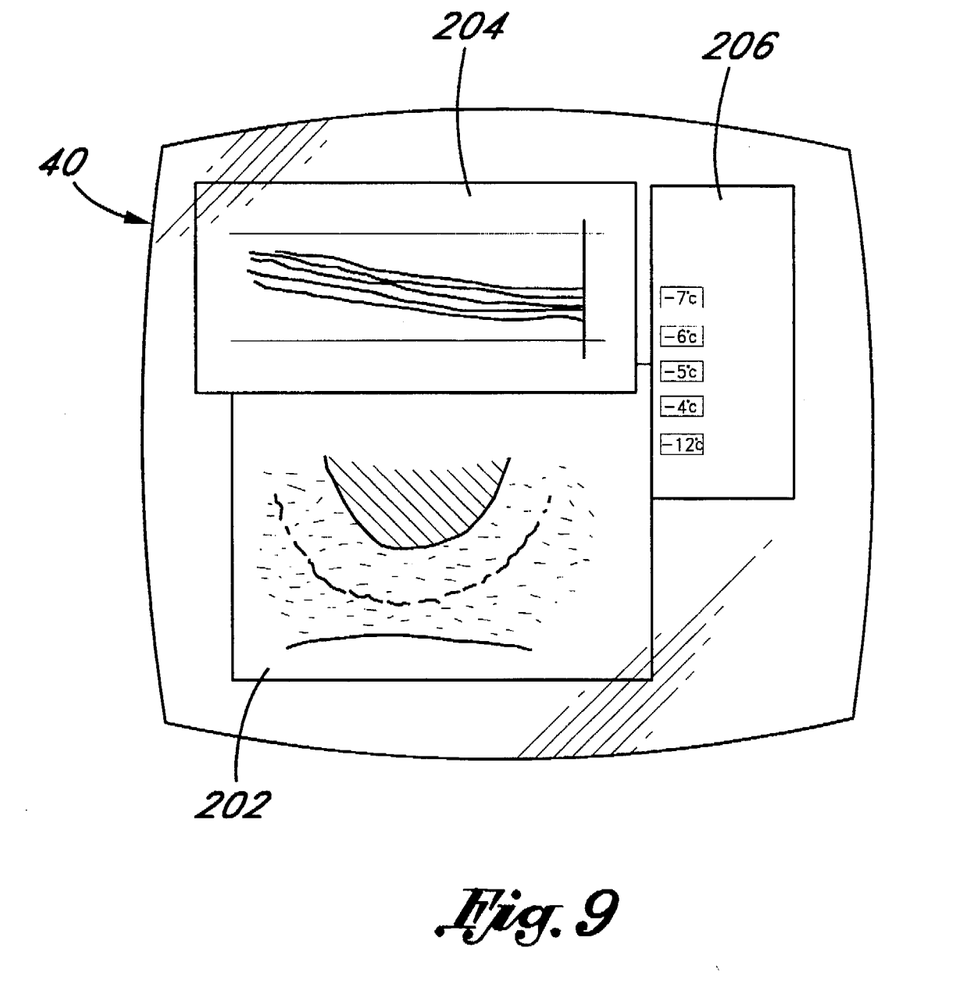
FIG. 9 is illustrates the preferred form of visual display produced by the system.

After placement of the probes, the cryogenic system 2 is actuated to gradually cause an ice ball to form and completely envelope the prostate gland. As this ice ball is forming, its nature and shape is displayed on monitor 40 as generally indicated in the image or visual field presented in FIG. 9. Specifically, in the preferred arrangement an ultrasonic image window 202 is provided that shows, as a blackened area, the gradual growth of the ice ball. Window area 204 preferably also is provided, this window area presenting the equivalent of a strip chart display of the recent temperatures detected by the various temperature probes 36 connected to acquisition system 32. Also, preferably in a window area such as at 206 various current temperature readings and other information are presented to the user of the system. Thus, the various controls of cryogenic control system 6 may be manipulated to cause the ice ball to gradually grow and to sculpt the fatal temperature region to the shape of the gland, thereby to cryogenically kill the prostate gland. If desired, control system 6 also may be connected to data processor 30 to provide information about the degree of cooling being applied to and by the various cryogenic probes, and this information used to predict placement of the cryo probes and the extent of cooling (or zone of fatal temperature) that will result. (This has not yet been done using the present system, but appears to be a likely extension of its capabilities.)

If the prostate is significantly enlarged, it may be necessary first to cause the ice ball to form in an area nearest bladder 64, then to move the cryogenic and temperature probes back somewhat to cause the ice ball to extend to the apex of the gland. Once the prostate gland or other defined internal region has been cooled to a fatal temperature, the cryosurgical system is shut down. After the ice ball has stopped growing the cooling probes may be removed and the temperature monitored until the ice ball gradually begins to dissipate. Then the temperature probes may be removed together with the ultrasonic probe to conclude the operation. Thereafter the patient will experience ablation of the tissue areas that have attained a fatal temperature. The system and procedure achieves radical cryosurgical ablation of the target area and gives positive assurance that a fatal temperature has been attained at the outer portions of the target area. It also permits the freezing zone to be sculpted for the desired pattern but to be terminated before freezing occurs beyond the target area.

Tests have indicated that this cryosurgical procedure is an effective modality for prostate carcinomas, even carcinoma modules extending somewhat beyond the prostate but connected to the prostate by the patient's circulatory system. Many believe that this procedure will replace radical prostectomy and other, similar procedures. The cryosurgical system and method, together with probes and improved guide, described herein provide a convenient and effective way to achieve such procedures.

Various changes and modifications in the preferred system and components can be envisioned. For example, a temperature and/or thermocouple probes may be curved to better treat better various organs such as tonsils and liver tissue. The temperature thermocouples may use "RTD" thermistors which are apparently even more reliable and accurate than thermocouples. The software and procedures for use may be modified to ensure accurate calibration of the thermocouples and data acquisition system. The cryogenic cooling system, and particularly its control system, may generate data that is supplied to the integrated data processor for display on monitor 40 and possibly even for prediction of the ice ball resulting from a particular application and cooling.

While a preferred embodiment of the invention has been described and illustrated, those skilled in this field may prefer modifications in this system, method and its components. For that reason the invention is defined by the following claims.

I claim:

1. A cryosurgical system for treating a defined internal area of a living body, the system including:

means for cryosurgically cooling a defined internal area of a living body;

means for measuring a temperature within the defined internal area of a living body as it is cryosurgically cooled by said cooling means, said temperature measuring means being spaced from said means for cryosurgically cooling;

means for illuminating the defined internal area of the living body as it is cooled by said means for cryosurgically cooling;

means for displaying an image of the living body area illuminated by the illuminating means as the defined internal area is cryosurgically cooled; and means connected to the temperature measuring means for displaying the temperature of the defined internal area of a living body as it is cryosurgically cooled;

whereby the defined internal area of a living body may be cryosurgically treated.

2. A cryosurgical system as set forth in claim 1 in which the image display means and the temperature display means present the separately displayed information in the same visual field.

3. A cryosurgical system as set forth in claim 1 in which the temperature display means presents the measured temperature at each successive moment over a predetermined time interval including a current interval.

4. A cryosurgical system as set forth in claim 3 in which the means for measuring temperature includes a plurality of percutaneous temperature probes.

5. A cryosurgical system as set forth in claim 1 in which the means for cooling a defined internal area cryosurgically kills tissue in the defined area.

6. A cryosurgical system as set forth in claim 4 in which the cooling means includes a plurality of percutaneous cooling probes to apply cryosurgical cooling to a non-spherical area defined by a number and placement of the probes in the defined internal area.

7. A cryosurgical system as set forth in claim 1 including means to maintain the temperature of at least a portion of the living body within the defined internal area.

8. A cryosurgical system as set forth in claim 1 including means to record the displayed image and the displayed temperature.

9. A cryosurgical system as set forth in claim 1 in which said means for illuminating the defined internal area ultrasonically illuminates the defined internal area, and said means for displaying an image of the illuminated area displays an ultrasonic image.

10. A cryosurgical system as set forth in claim 1 in which said means for measuring a temperature measures the temperature within the defined internal area of a living body at a location adjacent to a periphery of the defined internal area.

11. A cryosurgical system as set forth in claim 10 in which said means for measuring a temperature includes a plurality of percutaneous temperature probes, at least some of said probes being placed within the defined internal area of a living body at a location near the periphery of the defined internal area.

12. A cryosurgical system as set forth in claim 11 in which said means for illuminating a defined internal area ultrasonically illuminates the area, and in which the means for displaying an image displays an ultrasonic image of the illuminated area.

13. A cryosurgical system as set forth in claim 12 in which said means for cryosurgically cooling includes a plurality of percutaneous cooling probes, said system further including means to record the displayed ultrasonic image and the displayed temperature.

14. A method for cryosurgically treating a defined internal area of a living body comprising the steps of:

cooling a defined internal area of a living body;

measuring a temperature within the defined internal area as it is cooled; and ultrasonically illuminating the defined internal area as it is cooled;

thereby to monitor and control a degree of cooling applied to the defined internal area.

15. A cryosurgical method as set forth in claim 14 further including the step of displaying in the same visual field both an ultrasonic image of the illuminated area as it is cooled and the temperature of the defined internal area as it is cooled.

16. A cryosurgical method as set forth in claim 15 in which the displayed temperature includes a current temperature in multiple regions within the defined internal area.

17. A cryosurgical method as set forth in claim 15 in which the step of displaying the measured temperature displays the temperature at successive moments over a predetermined time interval including a current interval.

18. A cryosurgical method as set forth in claim 15 including the step of recording the displayed ultrasonic images and displayed temperatures.

19. A cryosurgical method as set forth in claim 14 in which the step of cooling a defined internal area cools at least a portion of the defined internal area to a fatal temperature.

20. A cryosurgical method as set forth in claim 14 in which the cooling step sculpts the cooling area to match the defined internal area.

21. A cryosurgical method as set forth in claim 14 further including the step of maintaining the temperature of at least a portion of the living body within the defined internal area.

* * * * *